United States Patent [19]
Sasisekharan et al.

[11] Patent Number: 5,714,376
[45] Date of Patent: Feb. 3, 1998

[54] HEPARINASE GENE FROM FLAVOBACTERIUM HEPARINUM

[75] Inventors: Ramnath Sasisekharan, Arlington, Mass.; Kelley Moremen, Athens, Ga.; Charles L. Cooney, Brookline, Mass.; Joseph J. Zimmermann, Elm Grove, Wis.; Robert S. Langer, Newton, Mass.

[73] Assignee: Massachusetts Institute of Technology, Cambridge, Mass.

[21] Appl. No.: 783,706

[22] Filed: Oct. 23, 1991

[51] Int. Cl.⁶ .............. C12N 15/60; C12N 1/21; C12N 9/88
[52] U.S. Cl. .............. 435/252.3; 435/2; 435/69.1; 435/69.8; 435/71.2; 435/172.3; 435/232; 435/320.1; 935/10; 935/14; 935/27; 935/56; 935/72
[58] Field of Search ............. 536/27, 23.2; 435/2, 435/69.1, 69.8, 71.2, 172.3, 232, 252.3, 320.1; 935/10, 14, 27, 56, 72

[56] References Cited

U.S. PATENT DOCUMENTS

| | | | |
|---|---|---|---|
| 4,338,401 | 7/1982 | Cremonesi | 435/178 |
| 4,341,869 | 7/1982 | Langer et al. | 435/232 |
| 4,373,023 | 2/1983 | Langer et al. | 435/2 |
| 4,401,758 | 8/1983 | Lormeau et al. | 435/884 |
| 4,795,703 | 1/1989 | Folkman et al. | 435/13 |
| 4,847,338 | 7/1989 | Linhardt et al. | 536/54 |
| 4,885,207 | 12/1989 | Johnson et al. | 428/403 |
| 5,013,724 | 5/1991 | Petitou et al. | 514/54 |

FOREIGN PATENT DOCUMENTS

| | | |
|---|---|---|
| 79107584 | 8/1979 | Japan . |
| 3108486 | 5/1991 | Japan . |

OTHER PUBLICATIONS

H. Bernstein, et al., "An Immobilized Heparinase System for Blood Deheparinization," in *Methods of Enzymology* vol. 137 (Academic Press, New York 1988) at pp. 515–519.

H. Bernstein, "A System for Heparin Removal," Ph. D. Dissertation, Massachusetts Insitute of Technology (1985).

S. E. Charm, et al., "Scale–Up of Protein Isolation," W. B. Jakoby, ed., *Methods in Enzymology* vol. 22 (Academic Press, New York 1971) at pp. 476, 490.

A. R. Comfort, et al., "The Influence of Bond Chemistry on Immobilized Enzyme Systems for Ex Vivo Use," *Biotechnology and Bioengineering* 32: 554–563 (Aug. 1988).

P. M. Galliher, et al. "Heparinase Production by Flavobacterium Heparinum," *Appl. Environ. Microbiol.* 41(2): 360–365 (Feb. 1981).

P. Hovingh, et al., "The Enzymatic Degradation of Heparin and Heparitin Sulfate," *The Journal of Biological Chemistry* 245(22): 6170–6175 (Nov. 1970).

M. D. Klein, et al., "Heparinase: In Vivo Activity and Immunogenicity in Rabbits," *J. Lab. Clin. Med.* 102(5): 828–837 (Nov. 1983).

R. Langer, et al., "An Enzymatic System for Removing Heparin in Extracorporeal Therapy," *Science* 217: 261–263 (Jul. 1982).

R. Langer, et al., "In Vivo Activity of Microbial Heparinase," *Trans Am. Soc. Artif. Intern. Organs* 28: 387–390 (1982).

R. J. Linhardt, et al., "An Immobilized Microbial Heparinase for Blood Deheparinization," *Applied Biochemistry and Biotechnology* 9: 41–55 (1984).

R. J. Linhardt, et al., "Immuno–Affinity Purification of Heparinase," *Int. J. Biochem.* 17(11): 1179–1183 (1985).

A. Linker, et al., "Heparinase and Heparitinase from Flavobacteria," V. Ginsburg, ed., *Methods in Enzymology*, vol. 28 (Academic Press, New York 1972) at pp. 902–911.

T. Nakamura, et al., "Purification and Properties of Bacteroides Heparinolyticus Heparinase (Heparin Lyase, EC 4.2.2.7)," *Journal of Clinical Microbiology* 26(5): 1070–1071 (May 1988).

N. Ototani, et al., "Purification of Heparinase and Heparitinase by Affinity Chromatography on Glycosaminoglycan–Bound AH–Sepharose 4B", *Carbohydrate Research* 88: 291–303 (1981).

W. R. Pitney, et al., "Control of Heparin Therapy," *British Medical Journal* 4: 139–141 (Oct. 1970).

M. E. Silva, et al., "Isolation and Partial Characterization of Three Induced Enzymes from Flavobacterium Heparinum Involved in the Degradation of Heparin and Heparitin Sulfates," *Biochemical and Biophysical Research Communications* 56(4): 965–972 (1974).

V. C. Yang, et al., "Purification and Characterization of Heparinase from Flavobacterium Heparinum," The Journal of *Biological Chemistry* 260(3): 1849–1857 (Feb. 1985).

V. Yang, et al., "Removal of the Anticoagulant Activities of the Low Molecular Weight Heparin Fractions and Fragments with Flavobacterial Heparinase," *Thrombosis Research* 44(5): 599–610 (1986).

Deutscher, M.P. (ed.) "Guide to Protein Purification" Methods in Enzymology vol. 182 pp. 603–613, 738–751.

Belyarsky et al. "PCR Based cDNA Library Construction: . . . " Nuc. Acids Res. vol. 17: 2919–2932 (Apr. 1989).

Cerbelaud, E.C. "Sulfur Regulation of Heparinase and Sulfatases . . . " Applied. Environ. Microbiol. 51: 640–646 (Mar. 1986).

Berger, S. et al. "Guide to Mol. Cloning Techniques" Meth in Enzymology vol. 152 pp. 393–399, 415–413, 432–447, 661–704 (1987).

*Primary Examiner*—Rebecca E. Prouty
*Attorney, Agent, or Firm*—Arnall Golden & Gregory, LLP

[57] ABSTRACT

The cloning of the heparinase gene from *Flavobacterium Heparinum* using the polymerase chain reaction is described. The Open Reading Frame (ORF) corresponded to 1152 base pairs encoding a precursor protein of MW 43,800 daltons. The amino acid sequence reveals a 20-residue leader peptide. The gene was expressed in two expression systems in *E. coli*.

9 Claims, 2 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 1379 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: YES ( i v ) ANTI-SENSE: YES ( v ) FRAGMENT TYPE: N-terminal ( v i ) ORIGINAL SOURCE:
( A ) ORGANISM: Flavobacterium heparinum ( x i ) SEQUENCE DESCRIPTION: SEQ ID NO:1:

```
CCTTTTGGGA GCAAAGGCAG AACCATCTCC GAACAAAGGC AGAACCAGCC TGTAAACAGA    60
CAGCAATTCA TCCGCTTTCA ACCAAAGTGA AAGCATTTAA TACAATACCA GAATGTCGCA   120
TTTCCCTTTC AGCGTACTTT TTGGGTAAAT AACCAATAAA AACTAAAGAC GGATGAAAAA   180
ACAAATTCTA TATCTGATTG TACTTCAGCA ACTGTTCCTC TGTTCGGCTT ACGCCCAGCA   240
AAAAAAATCC GGTAACATCC CTTACCGGGT AAATGTGCAG GCCGACAGTG CTAAGCAGAA   300
GGCGATTATT GACAACAAAT GGGTGGCAGT AGGCATCAAT AAACCTTATG CATTACAATA   360
TGACGATAAA CTGCGCTTTA ATGGAAAACC ATCCTATCGC TTTGAGCTTA AAGCCGAAGA   420
CAATTCGCTT GAAGGTTATG CTGCAGGAGA AACAAAGGGC CGTACAGAAT TGTCGTACAG   480
CTATGCAACC ACCAATGATT TTAAGAAATT TCCCCCAAGC GTATACCAAA ATGCGCAAAA   540
GCTAAAAACC GTTTATCATT ACGGCAAAGG GATTTGTGAA CAGGGGAGCT CCCGCAGCTA   600
TACCTTTTCA GTGTACATAC CCTCCTCCTT CCCCGACAAT GCGACTACTA TTTTTGCCCA   660
ATGGCATGGT GCACCCAGCA GAACGCTTGT AGCTACACCA GAGGGAGAAA TTAAAACACT   720
```

```
GAGCATAGAA GAGTTTTTGG CCTTATACGA CCGCATGATC TTCAAAAAAA ATATCGCCCA      780

TGATAAAGTT GAAAAAAAAG ATAAGGACGG AAAAATTACT TATGTAGCCG AAAGCCAAA       840

TGGCTGGAAG GTAGAACAAG GTGGTTATCC CACGCTGGCC TTTGGTTTTT CTAAAGGGTA      900

TTTTTACATC AAGGCAAACT CCGACCGGCA GTGGCTTACC GACAAAGCCG ACCGTAACAA      960

TGCCAATCCC GAGAATAGTG AAGTAATGAA GCCCTATTCC TCGGAATACA AAACTTCAAC     1020

CATTGCCTAT AAAATGCCCT TTGCCCAGTT CCCTAAAGAT TGCTGGATTA CTTTTGATGT     1080

CGCCATAGAC TGGACGAAAT ATGGAAAAGA GGCCAATACA ATTTTGAAAC CCGGTAAGCT     1140

GGATGTGATG ATGACTTATA CCAAGAATAA GAAACCACAA AAAGCGCATA TCGTAAACCA     1200

GCAGGAAATC CTGATCGGAC GTAACGATGA CGATGGCTAT TACTTCAAAT TTGGAATTTA     1260

CAGGGTCGGT AACAGCACGG TCCCGGTTAC TTATAACCTG AGCGGGTACA GCGAAACTGC     1320

CAGATAGCAA AAGCCCTAAG CGCATCCGAT AGGGCTTTTC TTATATTTAC AATAAAATT     1379
```

( 2 ) INFORMATION FOR SEQ ID NO:2:

( i ) SEQUENCE CHARACTERISTICS:
            ( A ) LENGTH: 384 amino acids
            ( B ) TYPE: amino acid
            ( C ) STRANDEDNESS: single
            ( D ) TOPOLOGY: linear ( i i ) MOLECULE TYPE: cDNA ( i i i ) HYPOTHETICAL: YES ( i v ) ANTI-SENSE: YES ( v ) FRAGMENT TYPE: N-terminal ( v i ) ORIGINAL SOURCE:
            ( A ) ORGANISM: Flavobacterium heparinum ( x i ) SEQUENCE DESCRIPTION: SEQ ID NO:2:

```
Met Lys Lys Gln Ile Leu Tyr Leu Ile Val Leu Gln Gln Leu Phe Leu
 1               5                  10                  15

Cys Ser Ala Tyr Ala Gln Gln Lys Lys Ser Gly Asn Ile Pro Tyr Arg
             20                  25                  30

Val Asn Val Gln Ala Asp Ser Ala Lys Gln Lys Ala Ile Ile Asp Asn
         35                  40                  45

Lys Trp Val Ala Val Gly Ile Asn Lys Pro Tyr Ala Leu Gln Tyr Asp
     50                  55                  60

Asp Lys Leu Arg Phe Asn Gly Lys Pro Ser Tyr Arg Phe Glu Leu Lys
 65                  70                  75                  80

Ala Glu Asp Asn Ser Leu Glu Gly Tyr Ala Ala Gly Glu Thr Lys Gly
                 85                  90                  95

Arg Thr Glu Leu Ser Tyr Ser Tyr Ala Thr Thr Asn Asp Phe Lys Lys
            100                 105                 110

Phe Pro Pro Ser Val Tyr Gln Asn Ala Gln Lys Leu Lys Thr Val Tyr
        115                 120                 125

His Tyr Gly Lys Gly Ile Cys Glu Gln Gly Ser Ser Arg Ser Tyr Thr
    130                 135                 140

Phe Ser Val Tyr Ile Pro Ser Ser Phe Pro Asp Asn Ala Thr Thr Ile
145                 150                 155                 160

Phe Ala Gln Trp His Gly Ala Pro Ser Arg Thr Leu Val Ala Thr Pro
                165                 170                 175

Glu Gly Glu Ile Lys Thr Leu Ser Ile Glu Glu Phe Leu Ala Leu Tyr
            180                 185                 190
```

| | | | | | | | | | | | | | |
|---|---|---|---|---|---|---|---|---|---|---|---|---|---|
| Asp | Arg | Met 195 | Ile | Phe | Lys | Lys | Asn 200 | Ile | Ala | His | Asp | Lys 205 | Val | Glu | Lys |
| Lys | Asp 210 | Lys | Asp | Gly | Lys | Ile 215 | Thr | Tyr | Val | Ala | Gly 220 | Lys | Pro | Asn | Gly |
| Trp 225 | Lys | Val | Glu | Gln | Gly 230 | Gly | Tyr | Pro | Thr | Leu 235 | Ala | Phe | Gly | Phe | Ser 240 |
| Lys | Gly | Tyr | Phe | Tyr 245 | Ile | Lys | Ala | Asn | Ser 250 | Asp | Arg | Gln | Trp | Leu 255 | Thr |
| Asp | Lys | Ala | Asp 260 | Arg | Asn | Asn | Ala | Asn 265 | Pro | Glu | Asn | Ser | Glu 270 | Val | Met |
| Lys | Pro | Tyr 275 | Ser | Ser | Glu | Tyr | Lys 280 | Thr | Ser | Thr | Ile | Ala 285 | Tyr | Lys | Met |
| Pro | Phe 290 | Ala | Gln | Phe | Pro | Lys 295 | Asp | Cys | Trp | Ile | Thr 300 | Phe | Asp | Val | Ala |
| Ile 305 | Asp | Trp | Thr | Lys | Tyr 310 | Gly | Lys | Glu | Ala | Asn 315 | Thr | Ile | Leu | Lys | Pro 320 |
| Gly | Lys | Leu | Asp | Val 325 | Met | Met | Thr | Tyr | Thr 330 | Lys | Asn | Lys | Lys | Pro 335 | Gln |
| Lys | Ala | His | Ile 340 | Val | Asn | Gln | Gln | Glu 345 | Ile | Leu | Ile | Gly | Arg 350 | Asn | Asp |
| Asp | Asp | Gly 355 | Tyr | Tyr | Phe | Lys | Phe 360 | Gly | Ile | Tyr | Arg | Val 365 | Gly | Asn | Ser |
| Thr | Val 370 | Pro | Val | Thr | Tyr | Asn 375 | Leu | Ser | Gly | Tyr | Ser 380 | Glu | Thr | Ala | Arg |

HEPARINASE GENE FROM FLAVOBACTERIUM HEPARINUM

BACKGROUND OF THE INVENTION

This invention is generally in the area of heparinases and is specifically directed to the gene encoding heparinase I, expressed in *Flavobacterium heparinum*.

The United States government has rights in this invention by virtue of grant number 25810 from the National Institutes of Health.

Heparin is an anticoagulant that activates serine protease inhibitors (serpins), which play a key role in the blood clotting cascade, as described by Damus et al., *Nature* 246:355–357 (1973). According to Lindahl et al., *Trends Biochem. Sci.* 11:221–225 (1986), heparin is the most acidic natural polymer known to date. It consists of a major 1,4-linked disaccharide repeating unit of D-uronic acid 1,4-β-D -glucosamine, and has an average of four negative charges (three sulfate groups and one carboxylate group) per monosaccharide unit. Heparin is both polydisperse, having an average molecular weight between 3,000 and 45,000 daltons, and heterogenous due to partial epimerization of D-glucuronic acid to L-iduronic acid and incomplete N- and O-sulfation, as reported by Kusche et al., *Proc. Natl. Acad. Sci.*, 77:6551–6555 (1980) and Comper, *Polymer Monograph* 7, 1981.

In addition, proteoglycans like heparin have a wide range of biological influences, including in blood chemistry, growth factor interaction and wound healing, interaction with basic structural proteins in the extracellular matrix and in cellular mediated immune responses. The basic nature of protein/peptide—heparin/complex carbohydrate interaction is important. Although heparin seems fairly heterogenous, it is now quite clear that different heparin fractions exhibit distinct and unique properties indicating some compositional and possibly structural specificity for its biological role, as reviewed by Cardin, A. D. and H. J. R. Weintraub, *Arteriosclerosis* 9, 21–32 (1989).

Heparinase, also referred to as heparin lyase, is the only known enzyme capable of degrading heparin that has been extensively characterized. It has been designated EC 4.2.2.7 by the Enzyme Commission. According to Galliher, et al., *Eur. J. Appl. Microbiol.* 15:252 (1982), the enzyme is a polysaccharide lyase found in the periplasmic space of *Flavobacterium heparinum*, a Gram-negative soil isolate. *F. heparinum* utilizes heparin as its sole source of carbon and nitrogen, as described by Hoving and Linker, *J. Biol. Chem.* 245:6170 (1970). Heparinase is the initial enzyme of heparin catabolism. Although constitutively expressed in low amounts, Galliher, et al., *App. Environ. Microbiol.* 41:360 (1981), have discovered that enzyme expression is induced by heparin and reversibly repressed by sulfate in the medium. Lindhardt, et al., *Appl. Biochem. Biotechnol.* 9:41 (1984), have shown that heparinase is inhibited by other polyanionic polysaccharides.

Heparinase has been purified by standard chromatographic techniques and its enzymatic properties characterized extensively, as described by scientists including Yang, et al., *J. Biol. Chem.* 260:1849 (1985). The enzyme is a 44,000 dalton monomeric protein with a pI of approximately 9.

Heparinase acts as an eliminase, leaving behind an unsaturated double bond at the non-reducing end group. This double bond is exploited in an assay for heparinase activity by the absorbance of the unsaturated product at 232 nm. The enzyme is marginally tolerant to salts and is very specific for heparin, having a $k_d$ of 30 nM. Heparinase has an activation energy of 4.5 kcal/mol, a km of $8\times10$-6 and a Vmax of $4\times10$-7M/min.

Heparin is often used in surgery to prevent blood clotting and to increase the compatibility of extracorporeal devices such as heart-lung and kidney dialysis machines. The enzymatic degradation of heparinbyheparinase is sufficient to eliminate the anticoagulation properties of heparin in surgery. As described by Langer, et al. in *Biomaterials: Interfacial Phenomenon and Applications, Adv. in Chem. Symposium Series*, Chap. 13, pp. 493–509 (1982), this property has led to the use of heparinase as an immobilized bioreactor in conjunction with heart-lung or kidney dialysis machines to deheparinize blood. Commercial application of the heparinase bioreactor is pending clinical trials.

A principal problem in the use of the heparinase bioreactor is the availability of sufficient amounts of pure heparinase to be immobilized onto a surface. This is primarily because the amount of heparinase constitutively expressed in *F. heparinum* is very low. Inducing expression of heparinase in *F. heparinum* with heparin is very expensive due to the amounts of heparin needed and the size of the fermentation to produce reasonable amounts of heparinase for any practical applications.

Cloning and expression of the heparinase gene is important in several ways. First, the only enzyme cloned and characterized to date which acts to depolymerise proteoglycans is heparinase. Second, heparin is the only anticoagulant commonly used in surgery so deheparinizing blood is an important medical problem. Moreover, heparinase catalyzed degradation of heparin into lower molecular weight heparin molecules can be used to yield products with specific anticoagulant activity, as discussed by Rosenfeld and Danishefsky, *Biochem. J.* 237:639–646 (1986).

Designing recombinant heparinases with altered activitie (s) would be interesting academically, as well as commercially. For example, heparinase can be used to deheparinize blood because the enzyme cleaves right at the AT-III binding oligomer. On the other hand, by further understanding the mechanism of the enzyme binding and depolymerizing heparin, recombinant heparinases with altered specificity could be designed, i.e. an AT-III binding heparin fragment not cleaved by the recombinant enzyme. This would be a very useful way of generating an AT-III binding heparin oligosaccharide, which currently is not available in large amounts, for use as an anticoagulant. Producing heparinases which could help and or improve in the enzyme purification or immobilization would also be quite valuable. For example, a tag (a particular peptide sequence) could be added at a region which does not alter the activity of the enzyme but makes the immobilization chemistry very efficient. This would help in improving enzyme loading onto the immobilization matrix.

It is therefore an object of the present invention to provide the gene encoding heparinase and a system for expression to facilitate the production of large amounts of heparinase.

It is another object of the present invention to provide methods and means for modifying the gene to produce recombinant heparinases having altered specificity and other desirable properties.

It is another object of the present invention to provide pure heparinase for use in the area of cytokine-proteoglycan interactions, as a tool or diagnostic as exemplified by fibroblast growth factor—heparin interactions.

SUMMARY OF THE INVENTION

The cloning of the heparinase gene from *Flavobacterium Heparinum* using the polymerase chain reaction is described. Two degenerate oligonucleotides, based on amino acid sequence derived from tryptic peptides of purified heparinase were used in the PCR with Flavobacterium genomic DNA as the template to generate a 600 base pairs probe. This probe was used to screen a pUC 18 Flavobacterium genomic library. The Open Reading Frame (ORF) corresponded to 1152 base pairs encoding a precursor protein of MW 43,800 daltons. Eleven different tryptic peptides (approximately 48% of the total amino acids) mapped into the ORF. The amino acid sequence reveals a 20-residue leader peptide.

Heparinase can be expressed from the gene. Additionally, the gene can be modified to produce heparinase with altered enzymatic activity, specificity, or binding properties. The sequence can also be used as a probe in the isolation of genes encoding other related enzymes.

The 600 basepair PCR product was used as a template with D and C as primers to generate the 160 basepair D:C product.

Figure 2:
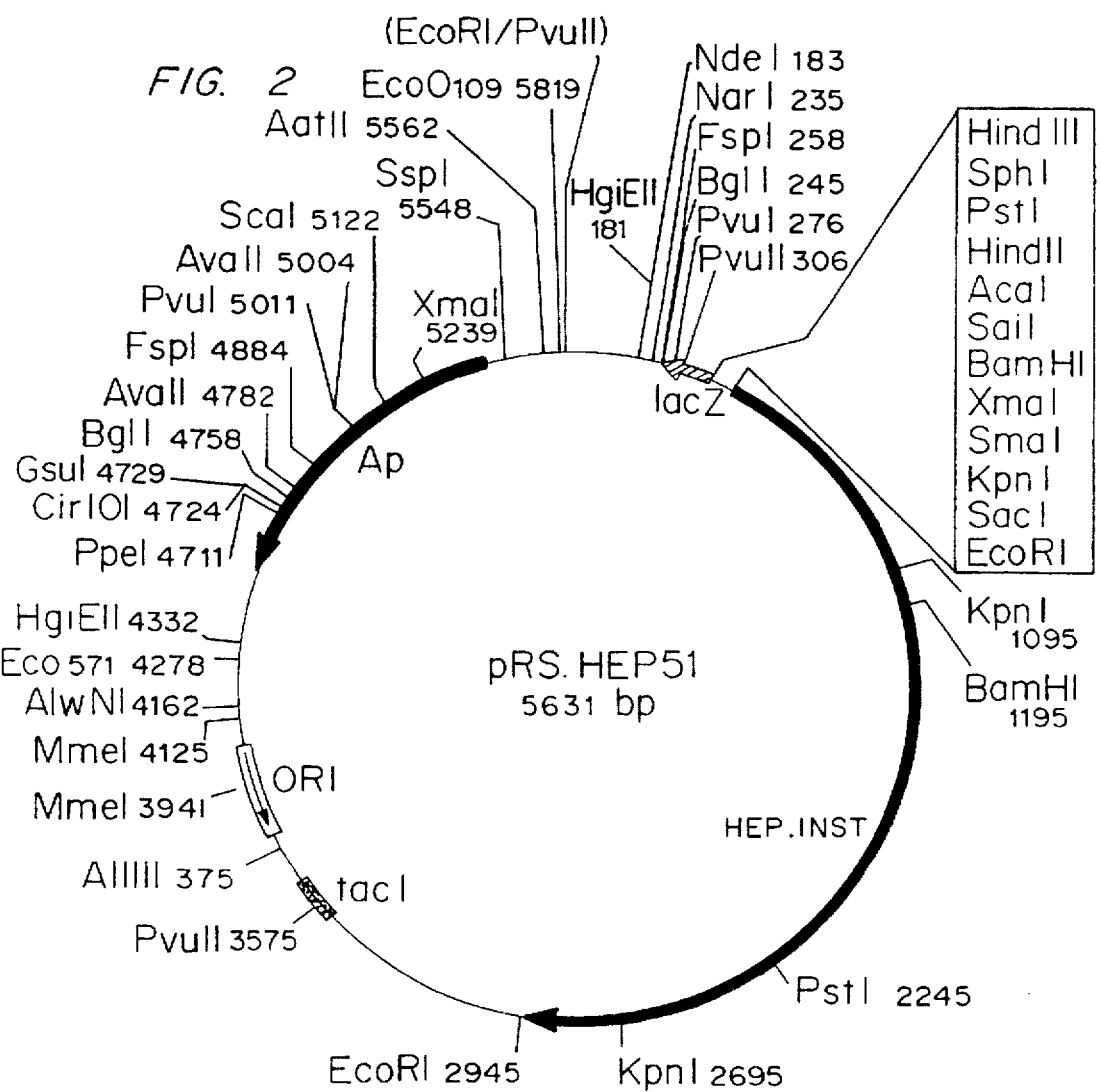

FIG. 2 is the restriction map of the genomic DNA pUC 18 plasmid, pRS.HEP51, having an insert containing the heparinase gene. The plasmid is 5631 bases long and has approximately 2300 bases of insert. The heparinase gene is in the Kpn I-KpnI fragment.

Figure 3:
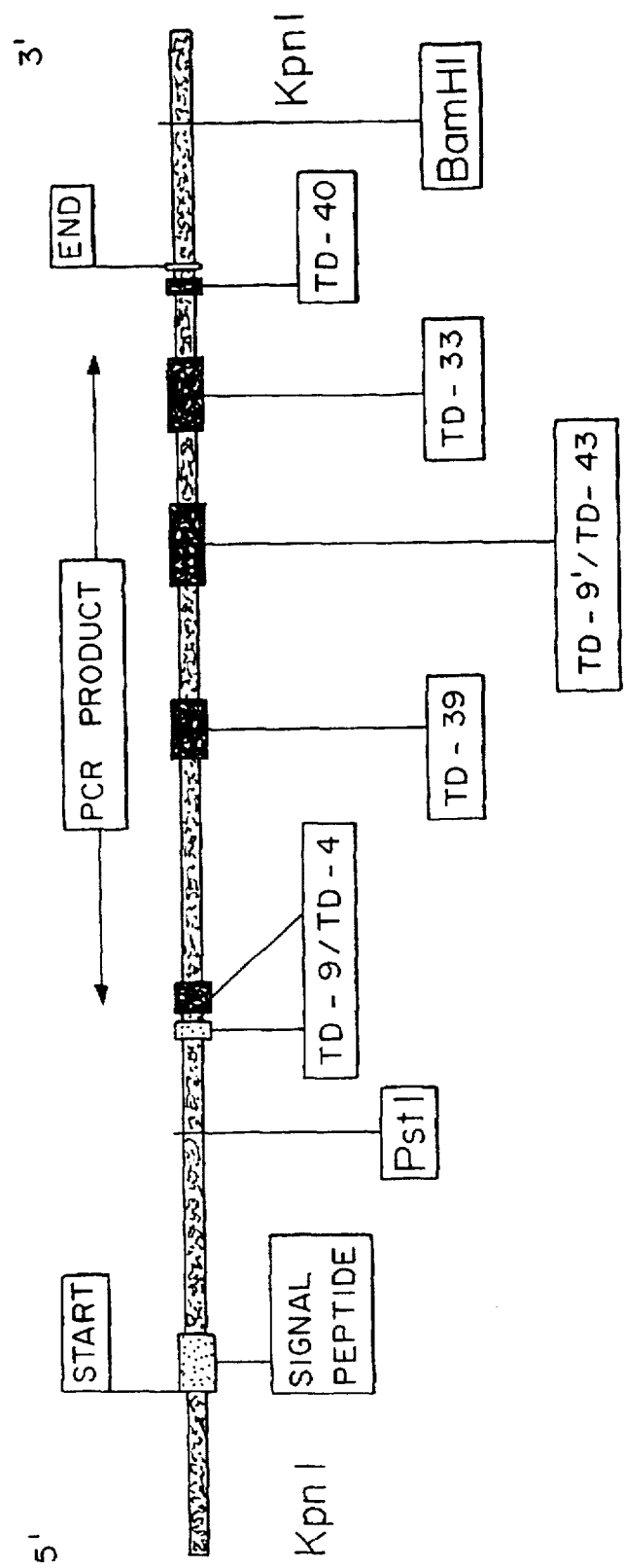

FIG. 3 is a KpnI-KpnI fragment map showing the heparinase gene structure with the different tryptic peptides mapping into the open reading frame. Six different peptides mapped into the heparinase gene translation region.

DETAILED DESCRIPTION OF THE INVENTION

The gene encoding heparinase in *F. heparinum* has been cloned. The nucleotide and amino acid sequences are shown below:

The following sequence (Sequence No. 1, base pairs 1 to 72, inclusive encodes a leader peptide:

| CCTTT | TGGGA | GCAAA | GGCAG | AACCA | TCTCC | GAACA | AAGGC | AGAAC | CAGCC | TGTAA |
|-------|-------|-------|-------|-------|-------|-------|-------|-------|-------|-------|
| ACAGA | CAGCA | ATTCA | TCCGC | TTTCA | ACCAA | AGTGA | AAGCA | TTTAA | TACAA | TACCA |
| GAATG | TCGCA | TTTCC | CTTTC | AGCGT | ACTTT | TTGGG | TAAAT | AACCA | ATAAA | AACTA |
| AAGAC | GG    |       |       |       |       |       |       |       |       |       |

The following sequence (Sequence No. 1, base pairs 173 to 1379, inclusive) encodes the heparinase:

| ATG | AAA | AAA | CAA | ATT | CTA | TAT | CTG | ATT | GTA | CTT | CAG | CAA | CTG | TTC | CTC |
|-----|-----|-----|-----|-----|-----|-----|-----|-----|-----|-----|-----|-----|-----|-----|-----|
| TGT | TCG | GCT | TAC | GCC | CAG | CAA | AAA | AAA | TCC | GGT | AAC | ATC | CCT | TAC | CGG |
| GTA | AAT | GTG | CAG | GCC | GAC | AGT | GCT | AAG | CAG | AAG | GCG | ATT | ATT | GAC | AAC |
| AAA | TGG | GTG | GCA | GTA | GGC | ATC | AAT | AAA | CCT | TAT | GCA | TTA | CAA | TAT | GAC |
| GAT | AAA | CTG | CGC | TTT | AAT | GGA | AAA | CCA | TCC | TAT | CGC | TTT | GAG | CTT | AAA |
| GCC | GAA | GAC | AAT | TCG | CTT | GAA | GGT | TAT | GCT | GCA | GGA | GAA | ACA | AAG | GGC |
| CGT | ACA | GAA | TTG | TCG | TAC | AGC | TAT | GCA | ACC | ACC | AAT | GAT | TTT | AAG | AAA |
| TTT | CCC | CCA | AGC | GTA | TAC | CAA | AAT | GCG | CAA | AAG | CTA | AAA | ACC | GTT | TAT |
| CAT | TAC | GGC | AAA | GGG | ATT | TGT | GAA | CAG | GGG | AGC | TCC | CGC | TAT | ACC |     |
| TTT | TCA | GTG | TAC | ATA | CCC | TCC | TCC | TTC | CCC | GAC | AAT | GCG | ACT | ACT | ATT |
| TTT | GCC | CAA | TGG | CAT | GGT | GCA | CCC | AGC | AGA | ACG | CTT | GTA | GCT | ACA | CCA |
| GAG | GGA | GAA | ATT | AAA | ACA | CTG | AGC | ATA | GAA | GAG | TTT | TTG | GCC | TTA | TAC |
| GAC | CGC | ATG | ATC | TTC | AAA | AAA | AAT | ATC | GCC | CAT | GAT | AAA | GTT | GAA | AAA |
| AAA | GAT | AAG | GAC | GGA | AAA | ATT | ACT | TAT | GTA | GCC | GGA | AAG | CCA | AAT | GGC |
| TGG | AAG | GTA | GAA | CAA | GGT | GGT | TAT | CCC | ACG | CTG | GCC | TTT | GGT | TTT | TCT |
| AAA | GGG | TAT | TTT | TAC | ATC | AAG | GCA | AAC | TCC | GAC | CGG | CAG | TGG | CTT | ACC |
| GAC | AAA | GCC | GAC | CGT | AAC | AAT | GCC | AAT | CCC | GAG | AAT | AGT | GAA | GTA | ATG |
| AAG | CCC | TAT | TCC | TCG | GAA | TAC | AAA | ACT | TCA | ACC | ATT | GCC | TAT | AAA | ATG |
| CCC | TTT | GCC | CAG | TTC | CCT | AAA | GAT | TGC | TGG | ATT | ACT | TTT | GAT | GTC | GCC |
| ATA | GAC | TGG | ACG | AAA | TAT | GGA | AAA | GAG | GCC | AAT | ACA | ATT | TTG | AAA | CCC |
| GGT | AAG | CTG | GAT | GTG | ATG | ATG | ACT | TAT | ACC | AAG | AAT | AAG | AAA | CCA | CAA |
| AAA | GCG | CAT | ATC | GTA | AAC | CAG | CAG | GAA | ATC | CTG | ATC | GGA | CGT | AAC | GAT |
| GAC | GAT | GGC | TAT | TAC | TTC | AAA | TTT | GGA | ATT | TAC | AGG | GTC | GGT | AAC | AGC |
| ACG | GTC | CCG | GTT | ACT | TAT | AAC | CTG | AGC | GGG | TAC | AGC | GAA | ACT | GCC | AGA |
| TAG | (stop codon) |

The following is the amino acid sequence (Sequence No. 2) of heparinase:

| Met | Lys | Lys | Gln | Ile | Leu | Tyr | Leu | Ile | Val | Leu | Gln | Gln | Leu | Phe | Leu |
|-----|-----|-----|-----|-----|-----|-----|-----|-----|-----|-----|-----|-----|-----|-----|-----|
| Cys | Ser | Ala | Tyr | Ala | Gln | Gln | Lys | Lys | Ser | Gly | Asn | Ile | Pro | Tyr | Arg |
| Val | Asn | Val | Gln | Ala | Asp | Ser | Ala | Lys | Gln | Lys | Ala | Ile | Ile | Asp | Asn |
| Lys | Trp | Val | Ala | Val | Gly | Ile | Asn | Lys | Pro | Tyr | Ala | Leu | Gln | Tyr | Asp |
| Asp | Lys | Leu | Arg | Phe | Asn | Gly | Lys | Pro | Ser | Tyr | Arg | Phe | Glu | Leu | Lys |
| Ala | Glu | Asp | Asn | Ser | Leu | Glu | Gly | Tyr | Ala | Ala | Gly | Glu | Thr | Lys | Gly |
| Arg | Thr | Glu | Leu | Ser | Tyr | Ser | Tyr | Ala | Thr | Thr | Asn | Asp | Phe | Lys | Lys |

-continued

| Phe | Pro | Pro | Ser | Val | Tyr | Gln | Asn | Ala | Gln | Lys | Leu | Lys | Thr | Val | Tyr |
| His | Tyr | Gly | Lys | Gly | Ile | Cys | Glu | Gln | Gly | Ser | Ser | Arg | Ser | Tyr | Thr |
| Phe | Ser | Val | Tyr | Ile | Pro | Ser | Ser | Phe | Pro | Asp | Asn | Ala | Thr | Thr | Ile |
| Phe | Ala | Gln | Trp | His | Gly | Ala | Pro | Ser | Arg | Thr | Leu | Val | Ala | Thr | Pro |
| Glu | Gly | Glu | Ile | Lys | Thr | Leu | Ser | Ile | Glu | Glu | Phe | Leu | Ala | Leu | Tyr |
| Asp | Arg | Met | Ile | Phe | Lys | Lys | Asn | Ile | Ala | His | Asp | Lys | Val | Glu | Lys |
| Lys | Asp | Lys | Asp | Gly | Lys | Ile | Thr | Tyr | Val | Ala | Gly | Lys | Pro | Asn | Gly |
| Trp | Lys | Val | Glu | Gln | Gly | Gly | Tyr | Pro | Thr | Leu | Ala | Phe | Gly | Phe | Ser |
| Lys | Gly | Tyr | Phe | Tyr | Ile | Lys | Ala | Asn | Ser | Asp | Arg | Gln | Trp | Leu | Thr |
| Asp | Lys | Ala | Asp | Arg | Asn | Asn | Ala | Asn | Pro | Glu | Asn | Ser | Glu | Val | Met |
| Lys | Pro | Tyr | Ser | Ser | Glu | Tyr | Lys | Thr | Ser | Thr | Ile | Ala | Tyr | Lys | Met |
| Pro | Phe | Ala | Gln | Phe | Pro | Lys | Asp | Cys | Trp | Ile | Thr | Phe | Asp | Val | Ala |
| Ile | Asp | Trp | Thr | Lys | Tyr | Gly | Lys | Glu | Ala | Asn | Thr | Ile | Leu | Lys | Pro |
| Gly | Lys | Leu | Asp | Val | Met | Met | Thr | Tyr | Thr | Lys | Asn | Lys | Lys | Pro | Gln |
| Lys | Ala | His | Ile | Val | Asn | Gln | Gln | Glu | Ile | Leu | Ile | Gly | Arg | Asn | Asp |
| Asp | Asp | Gly | Tyr | Tyr | Phe | Lys | Phe | Gly | Ile | Tyr | Arg | Val | Gly | Asn | Ser |
| Thr | Val | Pro | Val | Thr | Tyr | Asn | Leu | Ser | Gly | Tyr | Ser | Glu | Thr | Ala | Arg. |

EXAMPLE 1

Isolation and Analysis of cDNA Encoding Heparinase in *F. heparinum*

Because preliminary cloning attempts by others utilizing 1) antibody screening, 2) screening for functionally active heparinase in *E. coli* and 3) screening for the heparinase gene using probes derived from protein sequences regenerated by cyanogen bromine (CNBr) chemical digest were unsuccessful, the polymerase chain reaction was used to clone the heparinase gene. The reverse phase purified heparinase was reduced, alkylated and digested with trypsin to obtain approximately 60 peptide peaks which were separated and collected by reverse phase HPLC monitored at 210 nm and at 277 nm (for tyrosine and tryptophan), as described below.

Tryptic Digest and Protein Sequence Analyses

Heparinase was purified as described by Dietrich et al., *J. Biol. Chem.* 248:6408 (1973), Otatani et al., *Carbohyd. Res.* 88:291 (1981), and Yang et al., *J. Biol. Chem.* 260:1849 (1985), which are incorporated by reference herein. A final purification step was carried out by High Performance Liquid Chromatography (HPLC) using a reverse phase column that exploits the hydrophobic residues of the protein. A nanomole (approximately 45 µg) of the purified enzyme was denatured in 50 µl of an 8M urea, 0.4M ammonium carbonate solution, reduced with 5 mM dithiothreitol (DTT) at 50° C., cooled to room temperature, and alkylated with 10 mM iodoacetamide for 15 minutes in the dark. The total reaction volume was 200 µl. To this reaction mixture, ½5th w/w of trypsin was added and digestion carried out at 37° C. for 24 hour. The reaction was terminated by heating the sample at 65° C. for 2 minutes. The digest was separated by reverse phase HPLC using a gradient of 0 to 80% acetonitrile. The tryptic peptides were monitored at 210 and 277 nm.

The tryptic peaks were collected in Eppendorff tubes. Based on the homogeneity of the peptide peak, eight different peaks were sequenced using an Applied Biosystems sequencer, model 477, with an on-line model 120 PTH amino acid analyzer located in the Biopolymers lab, Center for Cancer Research, MIT. The sequences are set forth in Table I below. The designation (K,R) is used in Table I to indicate that trypsin cuts at either lysine or arginine residues. The asterisks in Table I represent amino acids that could not be determined. The peptide designated td Lx is the longest peptide sequenced having 38 residues. Native undigested heparinase was also sequenced to determined the N-terminus amino acids.

TABLE I

Sequences of Tryptic Peptides of Heparinase

| Peptide | Amino Acid Sequence |
|---------|---------------------|
| td 04 | (K, R) G I C E Q G S S R |
| td 09 | (K, R) T V Y H Y G K |
| td 09' | (K, R) T S T I A Y K |
| td 21 | (K, R) F G I Y R |
| td 33 | (K, R) A D I V N Q Q E I L I G R D D * G Y Y F K |
| td 39 | (K, R) I T Y V A G K P N G N K V E Q G G Y P T L A F * |
| td 43 | (K, R) M P F A Q F P K D C W I T F D V A I D * T K |
| td 40 | (K, R) N L S G Y S E T A R |
| tdm4 | K N I A H D K V E K K |
| td 72 | K T L S I E E F L A L Y D R |
| td Lx | R S Y T F S V Y I P S S F P D N A T T I F A Q W H G A P S R T L V T P E I K |

Three sets of primers were designed and synthesized, as shown in Table II. Primers were synthesized with an Applied Biosystems sequencer, model 477, with an on-line model 120 PTH amino acid analyzer located in the Biopolymers lab, Center for Cancer Research, MIT. These primer sets were used in the PCR amplification system for cloning the heparinase gene. The symbol "I" represents the nucleotide inosine. The amino acids of each peptide, depicted in boldface type, represent the residues chosen for the primer design. Two different sets of primers were constructed for tryptic peptide 33 to reduce the degree of inosine substitution at the 3' end of the primer.

TABLE II

Heparinase Primer Design

Peptide: td 04

Amino Acid Sequence:
  K G I C E Q G S S R primers:
  y1 5'- AAA GGI AT(T/C/A) TG(T/C) GA(A/G) CA(A/G) GG -3' y2 5'- CC (C/T)TG (C/T)TC (G/A)CA (T/G/A)AT ICC TTT -3'

Peptide: td 43

Amino Acid Sequence:
  (K, R) M P F A Q F P K D E W I T F C V A I D

TABLE II-continued

Heparinase Primer Design

*T K
primers:
D 5'- ATG CCI TT(T/C) GCI CA(A/G) TT(T/C) CCI AA(A/G) GA(T/C) GA -3'

E 3'- TAC GGI AA(A/G) CGI GT(T/C) AA(A/G) GGI TT(T/C) CT(A/G) CT -5'

Peptide: td 33

Amino Acid Sequence:
(K, R) A D I V N Q Q E I L I G R D D * G Y Y F K A
primers:
A 5'- ATI AA(T/C) CA(A/G) GA(A/G)ATI (C/T)TI AT(T/C/A) GG -3'

B 5'- CCIATIA(G/A) IAT (T/C)TC (T/C)TG (T/C)TG (A/G)TT ICA (A/C)AT

C 5'- CCIATIA(G/A) IAT (T/C)TC (T/CTG (T/C)TG (A/G)TT ICA (T/G)AT -3'

---

Of the six RHPLC peaks initially sequenced (Table I), three were chosen for primer design. Three sets of primers were designed (Table II). The PCR product of the combination the primers td43 and td33 was about 150 base pairs in length. The combination of td4 and td33 primers were about 600 base pairs. Primer td43 was 5' to primer td33 and primer td4 was 5' to td43 primer. Using the PCR product of td4 and td33 as a template and td43 and td4 as primers the predicted 150 base pair product was obtained confirming that td43 was between td4 and td33.

Figure 1:
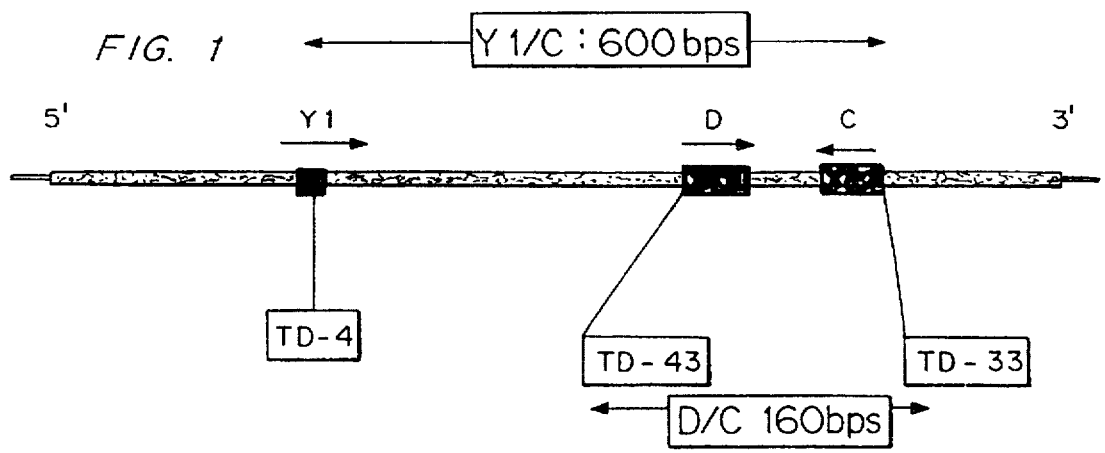
FIG. 1 is a schematic representation of the PCR products Y1:C and D:C which are 600 and 160 basepairs, respectively.

The 600 basepair product shown in FIG. 1 represents about 51% of the approximated total 1170 base pairs for the heparinase gene, assuming 43,000 dalton for heparinase and a 110 dalton average amino acid with a molecular weight corresponding to about 390 amino acids times three which is 1170 bases.

The 600 base pair probe was chosen for screening a pUC 18 library by high stringency colony hybridization. Two positive clones were identified which were carried through for three rounds of colony purification.

Genomic DNA, RNA, and Plasmid Library

The *F. heparinum* genomic DNA was isolated by the A.S.A.P.™ kit (Boehringer Mannheim, Indianapolis, Ind.) with the following modifications. The DNA was desalted over a Sephadex™ G-50 column (Nick column, Pharmacia, Piscataway, N.J.) and concentrated using a Centricon™ P-30 (Amicon Division, Beverly, Mass.) to a final volume of 100 l. From $1 \times 10^9$ cells, 105–115 g of DNA typically were obtained. Total cellular mRNA was isolated using the guanidine thiocyanate procedure set forth in the Promega technical information publication TB 087 December 1989, Promega Corp. Madison, Wis. 53711. A pUC 18 plasmid was obtained from Dr. A. J. Sinskey, of the Department of Biology at the Massachusetts Institute of Technology. The library was constructed using the *F. heparinum* genomic DNA. The genomic DNA was sonicated and modified by adding EcoRI linkers and then ligated to the pUC 18 vector. DH5a was transformed with the pUC 18 genomic library.

Amplification of the PCR Product

Amplification of the heparinase tryptic digest primers was carried out in a 25 l reaction volume containing 50 mM KCl, 10 mM Tris HCl (pH 8.3), 1.5 mM $MgCl_2$ and 0.01% gelatin plus the four deoxyribose nucleotide triphosphates (dNTPs) at 200M, using 0.5M primer and 3 l of the genomic DNA as the template, 2.5 units of the Taq polymerase (Cetus Corp., Emeryville, Calif.) and 25 l of mineral oil. The samples were placed on an automated heating block (DNA thermal cycler, Perkin Elmer Corp., Norwalk, Conn.) programmed for step cycles of temperatures 92° C. (2 minutes), 50° C. (1 minute) and 72° C. (3 minutes). This cycle was repeated 35 times. The final cycle had a 72° C. 10 minute extension. The PCR products were analysed on a 0.8% agarose gel containing 0.6 μg/ml ethidium bromide. The control reaction was provided by the Cetus kit.

Screening of the *Flavobacterium heparinum* pUC 18 Genomic Library

The pUC 18 library was titered to give approximately 1500 colonies to be tested by the probe generated by PCR. Each plate had approximately 100 colonies which were grown directly on nitrocellulose, to an appropriate small size, and then duplicated to be grown further overnight.

The PCR probe was labelled using the Random Hexanucleotide™ kit (RHN) (IBI Biochemicals Ltd.) which is described briefly as follows. One microgram DNA from the PCR product run was isolated from a low melt agarose gel, denatured by boiling at 95° C. for 10 minutes, and then chilled on ice. To the denatured DNA were added 10 mMdNTPs (dATP, dGTP, dCTP, dTTP), random hexanucleotides in the reaction buffer, and 50 μCi of $^{32}$PdCTP (3000 Ci/mmole). The reaction was carried with Klenow for 30 minutes at 37° C. and terminated using 0.2M EDTA. Following the labelling reaction, the labelled probe was purified from the free nucleotide by using a Sephadex G-50 column (Nick Column, Pharmacia, Piscataway, N.J.).

The colonies were screened with the labelled probe using standard colony hybridization procedures as described by Maniatis et al., *Molecular Cloning: A Laboratory Manual*, Cold Spring Harbor Laboratory, Cold Spring Harbor, N.Y., incorporated herein by reference.

Two positive clones were isolated and the plasmids tested for their ability to generate the 600 basepair PCR product. Both of the clones tested positive and were further characterized by restriction mapping. Clone pRS Hep 51 is a 2.3 kb insert in pUC 18 (shown in FIG. 2) with a Kpn-Kpn fragment of about 1.6 kb. This fragment was a positive template for generating a 600 basepair PCR product. The KpnI-KpnI fragment of pRS 51 was subcloned into M13 and sequenced.

DNA Sequencing

DNA sequencing was performed using phage M13 and employing the dideoxyadenosine 5'-alpha-$^{35}$S-triphosphate and Sequenase (U.S. Biochemical Corp, Cleveland, Ohio) as described by the manufacturer. The sequence data was obtained using successive nested deletions in M13 using T4 DNA polymerase as per Cyclone I Biosystems (International Biotechnologies Inc., New Haven, Conn.) or sequenced using synthetic oligonucleotide primers.

The sequence reveals a single, continuous open reading frame (ORF) of 1152 basepairs corresponding to 384 amino acids and a leader sequence of about 21 amino acids. The PCR product spans from 566 to 1216 bases from the start site and corresponds to about 57% of the total gene.

Initially six different tryptic peptides mapped into the ORF. Subsequently, five other peptides were sequenced for structural studies and all of them mapped into the ORF, for a total of about 48% of the total 367 amino acids. There are three cysteines in all, one associated with the signal peptide. The signal peptide is typical of prokaryotic sequences, having a charged N-terminal region, a core hydrophobic region and a cleavage region with a standard Ala.xxx.Ala site for cleavage.

EXAMPLE 2

Expression of the Heparinase Gene in *E. coli*

Two different expression systems were selected for the expression of heparinase in *E. coli:* the Omp A expression system and the pKK hyper-expression system. The plasmid designs for both expression systems are shown in Table III.

Omp A Expression System

The Omp A expression system secretes the protein of interest into the periplasmic space, as directed by the Omp A signal sequence, described by Ghrayeb, et al., *EMBO J.* 3:2437 (1984), incorporated herein by reference. This system was chosen since heparinase is naturally expressed into the periplasmic space of *F. heparinum*. The plasmid is under the control of the lac repressor and is induced by the addition of IPTG (isopropyl-β-D thiogalactoside) to the medium. The plasmid was inserted in the pIN-III Omp A-3 vector.

The heparinase insert was generated by PCR utilizing the N terminal and the C terminal sequences of heparinase with two appropriate restriction sites suitable for cloning into the EcoRI-BamHI sites. Two primers were constructed as shown in Table II. The insert was amplified by 5 cycles of PCR and ligated to the Omp A pIN vector with the *E. coli* periplasmic leader sequence. DH5α was transformed and expression was induced with 1 mM IPTG for 3–5 hours.

utilized by cloning the heparinase gene into a SmaI site, which is about 12 bases from the start codon ATG. Like the Omp A construction, the heparinase insert is obtained by PCR with SmaI and HindIII restriction sites at the N and the C terminals of the protein. As shown in Table III, the native heparinase leader sequence was used for over-production into the periplasm.

Periplasmic proteins of *E. coli* were isolated by osmotic shock. Briefly, 1.5 ml of cells were centrifuged after induction and washed with 10 mM Tris pH 7.5. The cells were then suspended in 20% sucrose in 10 mM Tris pH 7.5 and 5 μl of 0.5M EDTA. After a five minute incubation on ice, the cells were centrifuged and osmotically shocked by adding approximately 150 μl water. The periplasmic extract was used to determine enzyme activity. Heparinase activity was determined by monitoring the wavelength at 232 nm and by the Azure A methods of Bernstein et al., *Methods of Immunology* 137:515 (1988), incorporated herein by reference.

The periplasmic extracts were analyzed by sodium dodecyl sulfate-polyacrylamide gel electrophoresis (SDS-PAGE) using the method of Laemmli, *Nature* 227:690 (1974) and stained using Coumassie blue. In addition, a Western blot assay was performed to confirm the presence of heparinase using a heparinase monoclonal antibody. Heparinase was electrophoretically transferred from the SDS-PAGE gel onto nitrocellulose using the method of Gershoni and Palade, *Analytical Biochem.* 131:1 (1983), and then incubated with the monoclonal antibody. This antibody was stained using a secondary antibody conjugated to horseradish peroxidase.

TABLE III

Design of OmpA and pKK plasmids for Expression of Recombinant Heparinase in *E.coli*

Omp A secretion Expression system

```
N    Gly  Ile  Gln  Lys                Thr  Ala  Arg  End           C
XXX  GGA  ATT  CAG  AAA --------       ACT  GCC  AGA  TAG  GGATCC XXX
XXX  CCT  TAA  GTC  TTT --------       TGA  CGG  ACT  ATC  CCTAGG XXX
     EcoRI                                                      Bam HI
``` pKK over-Expression system

```
N    Met  Lys  Lys                Ala  Arg  End              C
XXX  TAA  CCC  GGG  ATG  AAA  AAA -----  GCC  AGA  TAG  AAG  CTT  CCG  XXX
XXX  ATT  GGC  CCC  TAC  TTT  TTT -----  CGG  TCT  ATC  TTC  GAA  GGC  XXX
          Sma I                                                  Hind III
```

As shown in Table III, the construct of the Omp A expression system results in two extra amino acids at the amino terminal of the heparinase gene, Gly and Ile. The heparinase sequence begins with a Gln.

The pKK Expression System

The pKK expression system is used for over-expression of proteins in accordance with the methods of Brosius and Holy, *Proc. Natl. Acad. Sci.*, 81:6929 (1984) and Jaffe et al., *Biochem.* 27:1869 (1988), incorporated by reference herein. This system contains a strong tac promotor which, in appropriate hosts, is regulated by the lac repressor and induced by the addition of IPTG, as in the Omp A system. The plasmid pKK223-3 has a pUC 8 multiple cloning site and a strong rrnB ribosomal terminator immediately following the tac promotor. The ribosomal binding site of the plasmid was

RNA Dot Blot Assay

The total cellular RNA was immobilized onto a Zeta probe™ membrane (Biorad, Richmond, Calif.) by alkaline RNA denaturation and fixation, and probed using the 600 base PCR product, used in screening for the heparinase gene. The hybridization was carried out with dot blot apparatus in accordance with the method of Thomas, *Proc. Natl. Acad Sci.* 77:5201 (1980). The RNA signal under different growth conditions has been investigated by Galliher, et al., *Eur. J. Appl. Microbiol.* (1982). It was established by those studies that heparinase at the protein level is optimally expressed under low sulphur conditions, which removes the requirement of heparin for induction. Heparinase mRNA signal under low sulphur growth conditions was therefore studied with and without heparin induction.

Both the OmpA and the pKK systems expressed heparinase. The OmpA system did not efficiently transport heparinase to the periplasm. For reasons not known, a large fraction of recombinant heparinase was retained in the cytoplasmic region along with the Omp A signal sequence. At lower temperatures (25°–30° C.) of growth, there was some secretion into the periplasmic space.

The pKK overproduction system produced heparinase only in the periplasmic space. The pKK system used the native *F. heparinum* heparinase leader sequence in which there was no problem with the transport of the recombinant protein with a foreign leader sequence. The pKK system expressed heparinase without any aberrant processing, although the expression was again optimal at lower temperatures. The presence of heparinase in the periplasm was confirmed by western blotting and by comparing in situ tryptic digest of the recombinant heparinase with that of the native heparinase, in terms of the peak profiles and some peaks which were isolated and sequenced.

A positive signal was obtained for the isolated *F. heparinum* nRNA using the 600 basepair probe derived from the PCR which has been used for isolating the heparinase gene, confirming that the gene isolated was a *F. heparinum* gene cloned in *E. coli.*

The expressed heparinase appeared to have at least some heparinase activity.

The sequence can be modified to alter specific enzymatic activity or binding specificity or affinity by substitution of one or more amino acids, using site directed mutagenesis or substitution of oligomers into the sequence encoding the heparinase. Methods and materials to accomplish this are known to those skilled in the art. The modified gene is then expressed and the product routinely screened for the altered activity.

Although described with reference to two specific expression systems, other expression systems are well known and commercially available. The heparinase gene can be expressed in these systems, using similar vectors and signal peptides or leader sequences.

Modifications and variations of the present invention will be obvious to those skilled in the art. Such modifications and variations are intended to come within the scope of the following claims.

We claim:

1. An isolated nucleic acid molecule encoding heparinase I produced by *Flavobacterium heparinum*.

2. The nucleic acid molecule of claim 1 having the nucleotide sequence (Sequence No. 1, base pairs 173 to 1324, inclusive) consisting essentially of:

| | | | | | | |
|---|---|---|---|---|---|---|
| | | | | | ATGAAAAA | 180 |
| ACAAATTCTA | TATCTGATTG | TACTTCAGCA | ACTGTTCCTC | TGTTCGGCTT | ACGCCCAGCA | 240 |
| AAAAAAATCC | GGTAACATCC | CTTACCGGGT | AAATGTGCAG | GCCGACAGTG | CTAAGCAGAA | 300 |
| GGCGATTATT | GACAACAAAT | GGGTGGCAGT | AGGCATCAAT | AAACCTTATG | CATTACAATA | 360 |
| TGACGATAAA | CTGCGCTTTA | ATGGAAAACC | ATCCTATCGC | TTTGGTTTTA | AAGCCGAAGA | 420 |
| CAATTCGCTT | GAAGGTTATG | CTGCAGGAGA | AACAAAGGGC | CGTACAGAAT | TGTCGTACAG | 480 |
| CTATGCAACC | ACCAATGATT | TTAAGAAATT | TCCCCCAAGC | GTATACCAAA | ATGCGCAAAA | 540 |
| GCTAAAAACC | GTTTATCATT | ACGGCAAAGG | GATTTGTGAA | CAGGGGAGCT | CCCGCAGCTA | 600 |
| TACCTTTTCA | GTGTACATAC | CCTCCTCCTT | CCCCGACAAT | GCGACTACTA | TTTTTGCCCA | 660 |
| ATGGCATGGT | GCACCCAGCA | GAACGCTTGT | AGCTACACCA | GAGGGAGAAA | TTAAAACACT | 720 |
| GAGCATAGAA | GAGTTTTTGG | CCTTATACGA | CCGCATGATC | TTCAAAAAAA | ATATCGCCCA | 780 |
| TGATAAAGTT | GAAAAAAAAG | ATAAGGACGG | AAAAATTACT | TATGTAGCCG | GAAAGCCAAA | 840 |
| TGGCTGGAAG | GTAGAACAAG | GTGGTTATCC | CACGCTGGCC | TTTGGTTTTT | CTAAAGGGTA | 900 |
| TTTTTACATC | AAGGCAAACT | CCGACCGGCA | GTGGCTTACC | GACAAAGCCG | ACCGTAACAA | 960 |
| TGCCAATCCC | GAGAATAGTG | AAGTAATGAA | GCCCTATTCC | TCGGAATACA | AAACTTCAAC | 1020 |
| CATTGCCTAT | AAAATGCCCT | TTGCCCAGTT | CCCTAAAGAT | TGCTGGATTA | CTTTTGATGT | 1080 |
| CGCCATAGAC | TGGACGAAAT | ATGGAAAAGA | GGCCAATACA | ATTTTGAAAC | CCGGTAAGCT | 1140 |
| GGATGTGATG | ATGACTTATA | CCAAGAATAA | GAAACCACAA | AAAGCGCATA | TCGTAAACCA | 1200 |
| GCAGGAAATC | CTGATCGGAC | GTAACGATGA | CGATGGCTAT | TACTTCAAAT | TTGGAATTTA | 1260 |
| CAGGGTCGGT | AACAGCACGG | TCCCGGTTAC | TTATAACCTG | AGCGGGTACA | GCGAAACTGC | 1320 |
| CAGA. | | | | | | |

3. The nucleic acid molecule of claim 1 encoding the amino acid sequence (Sequence No. 2) consisting essentially of:

| | | | | | | | | | | | | | | |
|---|---|---|---|---|---|---|---|---|---|---|---|---|---|---|
| Met 1 | Lys | Lys | Gln | Ile 5 | Leu | Tyr | Leu | Ile | Val 10 | Leu | Gln | Gln | Leu | Phe 15 | Leu |
| Cys | Ser | Ala | Tyr 20 | Ala | Gln | Gln | Lys | Lys 25 | Ser | Gly | Asn | Ile | Pro 30 | Tyr | Arg |

|     |     |     |     |     |     |     | -continued |     |     |     |     |     |     |     |
|---|---|---|---|---|---|---|---|---|---|---|---|---|---|---|
| Val | Asn | Val 35 | Gln | Ala | Asp | Ser | Ala 40 | Lys | Gln | Lys | Ala | Ile 45 | Ile | Asp | Asn |
| Lys | Trp 50 | Val | Ala | Val | Gly | Ile 55 | Asn | Lys | Pro | Tyr | Ala 60 | Leu | Gln | Tyr | Asp |
| Asp 65 | Lys | Leu | Arg | Phe | Asn 70 | Gly | Lys | Pro | Ser | Tyr 75 | Arg | Phe | Glu | Leu | Lys 80 |
| Ala | Glu | Asp | Asn | Ser 85 | Leu | Glu | Gly | Tyr | Ala 90 | Ala | Gly | Glu | Thr | Lys 95 | Gly |
| Arg | Thr | Glu | Leu 100 | Ser | Tyr | Ser | Tyr | Ala 105 | Thr | Thr | Asn | Asp | Phe 110 | Lys | Lys |
| Phe | Pro | Pro 115 | Ser | Val | Tyr | Gln | Asn 120 | Ala | Gln | Lys | Leu | Lys 125 | Thr | Val | Tyr |
| His | Tyr 130 | Gly | Lys | Gly | Ile | Cys 135 | Glu | Gln | Gly | Ser | Ser 140 | Arg | Ser | Tyr | Thr |
| Phe 145 | Ser | Val | Tyr | Ile | Pro 150 | Ser | Ser | Phe | Pro | Asp 155 | Asn | Ala | Thr | Thr | Ile 160 |
| Phe | Ala | Gln | Trp | His 165 | Gly | Ala | Pro | Ser | Arg 170 | Thr | Leu | Val | Ala | Thr 175 | Pro |
| Glu | Gly | Glu | Ile 180 | Lys | Thr | Leu | Ser | Ile 185 | Glu | Glu | Phe | Leu | Ala 190 | Leu | Tyr |
| Asp | Arg | Met 195 | Ile | Phe | Lys | Lys | Asn 200 | Ile | Ala | His | Asp | Lys 205 | Val | Glu | Lys |
| Lys | Asp 210 | Lys | Asp | Gly | Lys | Ile 215 | Thr | Tyr | Val | Ala | Gly 220 | Lys | Pro | Asn | Gly |
| Trp 225 | Lys | Val | Glu | Gln | Gly 230 | Gly | Tyr | Pro | Thr | Leu 235 | Ala | Phe | Gly | Phe | Ser 240 |
| Lys | Gly | Tyr | Phe | Tyr 245 | Ile | Lys | Ala | Asn | Ser 250 | Asp | Arg | Gln | Trp | Leu 255 | Thr |
| Asp | Lys | Ala | Asp 260 | Arg | Asn | Asn | Ala | Asn 265 | Pro | Glu | Asn | Ser | Glu 270 | Val | Met |
| Lys | Pro | Tyr 275 | Ser | Ser | Glu | Tyr | Lys 280 | Thr | Ser | Thr | Ile | Ala 285 | Tyr | Lys | Met |
| Pro | Phe 290 | Ala | Gln | Phe | Pro | Lys 295 | Asp | Cys | Trp | Ile | Thr 300 | Phe | Asp | Val | Ala |
| Ile 305 | Asp | Trp | Thr | Lys | Tyr 310 | Gly | Lys | Glu | Ala | Asn 315 | Thr | Ile | Leu | Lys | Pro 320 |
| Gly | Lys | Leu | Asp | Val 325 | Met | Met | Thr | Tyr | Thr 330 | Lys | Asn | Lys | Lys | Pro 335 | Gln |
| Lys | Ala | His | Ile 340 | Val | Asn | Gln | Gln | Glu 345 | Ile | Leu | Ile | Gly | Arg 350 | Asn | Asp |
| Asp | Asp | Gly 355 | Tyr | Tyr | Phe | Lys | Phe 360 | Gly | Ile | Tyr | Arg | Val 365 | Gly | Asn | Ser |
| Thr | Val 370 | Pro | Val | Thr | Tyr | Asn 375 | Leu | Ser | Gly | Tyr | Ser 380 | Glu | Thr | Ala | Arg. |

4. The nucleic acid molecule of claim 1 inserted into an expression vector.

5. The nucleic acid molecule of claim 1 directly associated with a nucleic acid fragment encoding a signal peptide.

6. The nucleic acid molecule of claim 5 wherein the signal peptide is encoded by the nucleic acid (Sequence No. 1, base pairs 1 to 172, inclusive) consisting essentially of:

| CCTTTTGGGA | GCAAAGGCAG | AACCATCTCC | GAACAAAGGC | AGAACCAGCC | TGTAAACAGA | 60 |
| CAGCAATTCA | TCCGCTTTCA | ACCAAAGTGA | AAGCATTTAA | TACAATACCA | GAATGTCGCA | 120 |
| TTTCCCTTTC | AGCGTACTTT | TTGGGTAAAT | AACCAATAAA | AACTAAAGAC | GA. | 180 |

7. The nucleic acid molecule of claim 5 wherein the signal peptide directs the transport of the protein from the cytoplasm to the periplasm.

8. The nucleic acid molecule of claim 1 in a procaryotic cell other than *F. heparinum* which is capable of expressing the molecule.

9. The nucleic acid molecule of claim 8 in a procaryotic cell cultured under low sulfate conditions which is capable of expressing the molecule.

* * * * *